(12) United States Patent
Ovchinnikova et al.

(10) Patent No.: US 9,297,828 B2
(45) Date of Patent: Mar. 29, 2016

(54) HIGH HEATING RATE THERMAL DESORPTION FOR MOLECULAR SURFACE SAMPLING

(71) Applicant: UT-BATTELLE, LLC, Oak Ridge, TN (US)

(72) Inventors: Olga S. Ovchinnikova, Knoxville, TN (US); Gary J. Van Berkel, Clinton, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 0 days.

(21) Appl. No.: 14/227,364

(22) Filed: Mar. 27, 2014

(65) Prior Publication Data

US 2015/0276559 A1    Oct. 1, 2015

(51) Int. Cl.
*G01Q 30/02* (2010.01)
*G01N 1/40* (2006.01)

(52) U.S. Cl.
CPC ............... *G01Q 30/02* (2013.01); *G01N 1/405* (2013.01); *G01N 1/4022* (2013.01)

(58) Field of Classification Search
None
See application file for complete search history.

(56) References Cited

U.S. PATENT DOCUMENTS

| | | | |
|---|---|---|---|
| 4,988,879 A * | 1/1991 | Zare | H01J 27/24 250/282 |
| 7,576,319 B2 | 8/2009 | Miller et al. | |
| 7,619,217 B2 * | 11/2009 | Shea | H01J 49/0463 250/281 |
| 7,694,346 B2 | 4/2010 | Adams et al. | |
| 7,952,068 B2 | 5/2011 | Caulfield et al. | |
| 7,972,865 B2 | 7/2011 | Yi et al. | |
| 8,242,459 B2 | 8/2012 | Sun et al. | |
| 8,468,611 B2 * | 6/2013 | Riedo | B82Y 10/00 427/226 |
| 2007/0295902 A1 * | 12/2007 | Shea | H01J 49/0454 250/288 |
| 2012/0074306 A1 * | 3/2012 | Jesse | B82Y 35/00 250/282 |
| 2012/0199735 A1 | 8/2012 | Krechmer et al. | |

FOREIGN PATENT DOCUMENTS

DE    3303400    8/1984

OTHER PUBLICATIONS

Anderson et al., "Mass Spectra of underivatized peptide amides related to substance P", Biochemical and Biophysical Research Communications (1977) 78(1): 372-376.

Brady et al., "Mass spectrometry of intact neutral macromolecules using intense non-resonant femtosecond laser vaporization with electrospray post-ionization", Rapid Commun. Mass Spectrom. (2009) 23: 3151-3157.

Chimmalgi et al., "Femtosecond laser aperturless near-field nanomachining of metals assisted by scanning probe microscopy", Appl Phys Lett (2003) 82(8): 1146-1148.

Handschuh, "Strategies for intact laser desorption", Eidgenossische Technische Hochschule Zurich, Dissertation (1999). (125 pages).

Karbach et al., "Matrix-assisted filament desorption/ionization mass spectrometry", J Am Soc Mass Spectrom (1998) 9: 1226-1228.

(Continued)

*Primary Examiner* — Andrew Smyth
(74) *Attorney, Agent, or Firm* — Novak Druce Connolly Bove + Quigg, LLP.

(57) ABSTRACT

A method for analyzing a sample having at least one analyte includes the step of heating the sample at a rate of at least $10^6$ K/s to thermally desorb at least one analyte from the sample. The desorbed analyte is collected. The analyte can then be analyzed.

23 Claims, 5 Drawing Sheets

(56) References Cited

OTHER PUBLICATIONS

Kasper, "Simultaneous nanothermal analysis using heated microcantilevers", University of Illinois, Thesis (2010). (36 pages).

King et al., "Nanoscale thermal analysis of an energetic material", Nano Lett (2006) 6(9): 2145-2149.

Lee et al., "Electrical, thermal, and mechanical characterization of silicon microcantilever heaters", Journal of Microelectromechanical Systems (2006) 15(6): 1644-1655.

Lu et al., "Laser-scanning probe microscope based nanoprocessing of electronics materials", Jpn J Appl Phys (2001) 40(Pt. 1 No. 6B): 4395-4398. (abstract only).

Maechiling et al., "Evidence for thermalization of surface-desorbed molecules at heating rates of 108 K/s", J Chem Phys (1996) 104(21): 8768-8776.

Mamin et al., "Thermomechanical writing with an atomic force microscope tip", Appl Phys Lett (1992) 61(8): 1003-1005.

Milner et al., "Floating tip nanolithography", Nano Lett (2008) 8(7): 2017-2022.

Milner et al., "Heating of an atomic force microscope tip by femtosecond laser pulses", Appl Phys A (2010) 99: 1-8.

Nettesheim et al., "Pulsed laser heating of surfaces: Nanosecond timescale temperature measurement using black body radiation", Chemical Physics Letters (1996) 255: 39-44.

Philippoz et al., "Pulsed heating of surfaces: Comparison between numerical stimulation, analytical models, and experiments", Chemical Physics Letters (1989) 158(1-2): 12-17.

Vertes et al., "Methods utilizing low and medium laser irradiance: A. laser-induced thermal desorption and matrix-assisted methods", Laser Ionization Mass Analysis (1993) 124(ch. 3): 127-175.

Vogel et al., "Mechanisms of pulsed laser ablation of biological tissues", Chem Rev (2003) 103(2): 577-644.

\* cited by examiner

HIGH HEATING RATE THERMAL DESORPTION FOR MOLECULAR SURFACE SAMPLING

STATEMENT REGARDING FEDERALLY SPONSORED RESEARCH

This invention was made with government support under contract No. DE-AC05-00OR22725 awarded by the U.S. Department of Energy. The government has certain rights in this invention.

FIELD OF THE INVENTION

This invention relates generally to surface sampling, and more particularly to surface sampling by thermal desorption.

BACKGROUND OF THE INVENTION

In general thermal desorption is limited to material with relatively high vapor pressure and a molecular weight of less than 500 Da. The lack in compound coverage in the types of molecular species that can be detected intact by mass spectrometry makes thermal desorption less of a universal surface sampling approach than laser based desorption approaches that have a much more broad compound coverage and are able to desorb polymers and proteins intact from a surface. However, laser desorption (nanosecond and picosecond pulse length laser ablation) at its core is inherently a thermal desorption process that happens on a very fast time scale $10^8$ to $10^{13}$ K/s and is commonly referred to as laser induced thermal desorption (LITD). Spatially resolved thermal desorption processes are described in Jesse et al U.S. Pat. No. 8,384,020 the disclosure of which is incorporated fully by reference.

Prior work has demonstrated that applying sufficiently high heating ramp rates to a tungsten wire filament will allow intact desorption of large biomolecules such as substance P, as well as melettin and valinomycin. See Anderson, W. R.; Frick, W.; Daves, G. D.; Barofsky, D. F.; Yamaguchi, I.; Chang, D.; Folker, K.; Rosell, S. "Mass Spectra of Underivatized Peptide Amides related to Substance P." *Biochem. Biophys. Res. Commun.*, 1977, 78, 372-376, and Karbach, V.; Knochenmuss, R.; Zenobi, R. "Matrix-Assisted Filament Desoption/Ionization Mass Spectrometry." *J. Am. Soc. Mass Spectrom.*, 1998, 9, 1226-1228.

The difficulty of reaching higher heating rates stems from the challenge of applying a voltage to the resistive element in a short enough times scale to heat it up to significantly high temperatures. Prof. William King at the University of Illinois-Urbana Champagne, who pioneered the technology behind the use of the thermal probes, has been able to heat cantilevers to over 833 K within 16 µs, by using electronics that have the power required to drive cantilevers at high speed and high power. See Lee, J.; Beechem, T.; Wright, T. L.; Nelson, B. A.; Graham, S.; King, W. P. "Electrical, Thermal, and Mechanical Characterization of Silicon Microcantilever Heaters." *J. Microelectromech. Syst.* 2006, 15, 1644-1655. The disclosures of all of the above references are hereby incorporated fully by reference.

SUMMARY OF THE INVENTION

A method for analyzing an analyte from a sample includes the step of heating the sample at a rate of at least $10^6$ K/s to thermally desorb at least one analyte from the sample. The desorbed analyte is collected. The analyte can then be analyzed.

The heating rate can be at least $10^{13}$ K/s. The heating rate can be between $10^6$-$10^{13}$ K/s.

The analyte can have a molecular weight of greater than 500 Da. The analyte can have a molecular weight greater than 1000 Da.

The heating step can be resistive heating. The heating can be by a probe having a resistive heating element. The probe can have a heating tip having a surface area of less than 1 µm$^2$. The tip can be silicon. The resistive heating element can be solid state. The probe can be an atomic force microscopy cantilever.

The method can further comprise the step of ionizing the analyte after the analyte is desorbed. The analyzing of the analyte can be performed by at least one selected from the group consisting of mass spectrometers, ionization sources, spectroscopy devices, and separation methods. When the desorption process is at or near atmospheric pressure, the ionization sources can be at least one selected from the group consisting of electrospray ionization (ESI), electrospray chemical ionization (ESCi), atmospheric pressure chemical ionization (APCI), atmospheric pressure photo-ionization (APPI), and inductively coupled plasma (ICP). If the desorption process is at vacuum or the desorbed material is transferred from atmospheric pressure to vacuum for ionization, suitable ionization techniques will include electron ionization (EI), chemical ionization (CI), and photoionization.

The separation method can be at least one selected from the group consisting of liquid chromatography, solid phase extraction, HPLC, capillary electrophoresis, ion mobility spectrometry and differential mobility spectrometry. The mass spectrometer can be at least one selected from the group consisting of sector MS, time-of-flight MS, quadrupole mass filter MS, three-dimensional quadrupole ion trap MS, linear quadrupole ion trap MS, Fourier transform ion cyclotron resonance MS, orbitrap MS, and toroidal ion trap MS.

A method for collecting a sample from a sample surface can include the step of heating the sample surface at a rate of at least $10^6$ K/s to thermally desorb at least one analyte from the sample surface. The desorbed analyte can then be collected.

A system for collecting a sample from a sample surface can include a tip having a heating device heating the tip at a rate of at least $10^6$ K/s to thermally desorb at least one analyte from the sample surface. A drive is provided for placing the tip into and out of contact with the surface. A means is provided for collecting the analyte. The heating device can include a resistive element. The heating device can include a laser.

BRIEF DESCRIPTION OF THE DRAWINGS

There are shown in the drawings embodiments that are presently preferred it being understood that the invention is not limited to the arrangements and instrumentalities shown, wherein:

FIG. 1 (a)-(d) is a schematic diagram of high heating rate thermal desorption tips utilizing (a) laser heated stationary; (b) pulsed resistive heating stationary; (c) continuously heated rapid tapping; and (d) sample removal followed by heating methodologies.

DETAILED DESCRIPTION OF THE INVENTION

A method for analyzing a sample having at least one analyte includes the step of heating the sample at a rate of at least $10^6$ K/s to thermally desorb the at least one analyte from the sample. The sample can be heated by a probe at a sample surface to desorb the analyte from the sample surface, or a portion of the sample can be removed by a probe and subsequently desorbed from the probe by the rapid heating of the invention. The desorbed analyte is collected. The analyte can then be analyzed. The heating rate can be at least $10^6$, $10^7$, $10^8$, $10^9$, $10^{10}$, $10^{11}$, $10^{12}$, or at least $10^{13}$ K/s. The heating rate can be any value between, and can be within a range of any high value and any low value between $10^6$-$10^{13}$ K/s. In another aspect, the heating rate can be any value between $10^9$-$10^{13}$ K/s.

The rapid heating of the invention preserves intact into the gas phase molecular species that would otherwise decompose upon heating. The fast rate of desorption will overcome the rate of decomposition of thermally labile species such that these species will desorb into the gas phase before they can thermally decompose. These heat-intact compounds can then be analyzed accurately. Some molecules like polyaromatic hydrocarbons or buckyballs are extremely thermally stable and thermal decomposition is not a problem. There are very many molecules that are not thermally stable, and for some heating even at low temperatures will result in decomposition. These thermally labile molecules are especially suited for the invention. The thermally labile characteristics of molecules relate to both mass and the types of chemical bonds in the compound. The invention is useful for molecules or compounds with chemical bonds that are thermally labile such that the molecule or compound cannot be desorbed into the gas phase even at low temperatures without chemical bond cleavage. Some general classes or compounds include macromolecular species like proteins and peptides, carbohydrates and simple sugars, and DNA and oligonucleotides. Synthetic macromolecules like polymers with thermally labile bonds and a number of smaller molecules with highly polar functional groups are also suitable for the invention. The analyte can have a molecular weight of greater than 500 Da. The analyte can have a molecular weight greater than 1000 Da.

The term "thermally labile" as used herein relates to molecular compounds or covalent bonds therein that are cleaved during the heating of the molecule, and where the activation energy for molecular desorption becomes larger than the bond dissociation energy of the molecule. Under these conditions, thermal decomposition will be favored over thermal desorption. Upon heating, a thermally labile molecule or the covalent bonds therein are broken. A thermally labile compound does not remain intact as a molecular species upon heating to a temperature at which the bonds therein are no longer stable. A thermally labile molecule will dissociate when the internal energy of the molecule caused by heating is distributed to particular bonds within the molecules are sufficient to break those covalent bonds. This dissociation can occur when the compound is heated to a desorption temperature.

Figure 7:
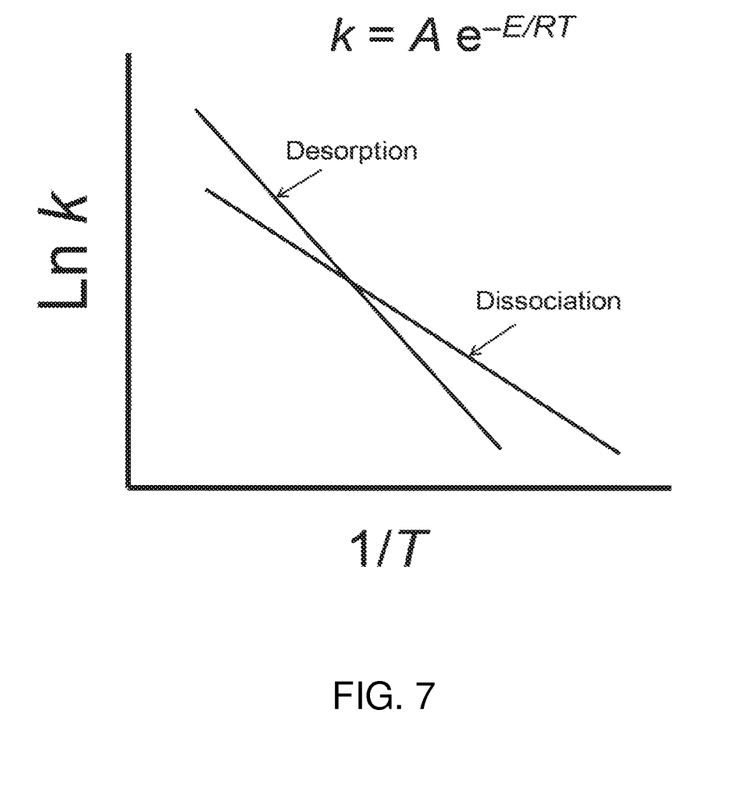
FIG. 7 is an Arrhenius plot for desorption of Ln k vs. 1/T.

The activation energy for desorption increases with the molecular size of analytes because of the stronger intermolecular interaction, such as the van der Waals forces, including hydrogen bonding. When the activation energy for molecular desorption becomes larger than the bond dissociation energy of the molecule, thermal decomposition will be favored over thermal desorption. Thermal desorption could become more favorable over the thermal decomposition at higher temperatures for molecular species even when the activation energy of desorption is larger than the bond dissociation energy. That this phenomenon is possible can be understood based the classic Arrhenius reaction rate theory for thermal desorption and decomposition, as illustrated in FIG. 7. Because the slope of the Arrhenius plot for desorption is steeper than that for thermal decomposition, the rate constant for thermal desorption can become larger than that for thermal decomposition in the higher temperature region. Raising the sample temperature at the very high rates of the invention will cause the rate of thermal desorption to supersede the rate of thermal decomposition. The temperature at which the Arrhenius plots for thermal desorption and decomposition intersect depends on the sample. In general the larger the size (mass) of the molecule, the higher the temperature for the intersection of the two Arrhenius plots, and higher heating rates will be required for desorption to dominate dissociation.

Figure 1:
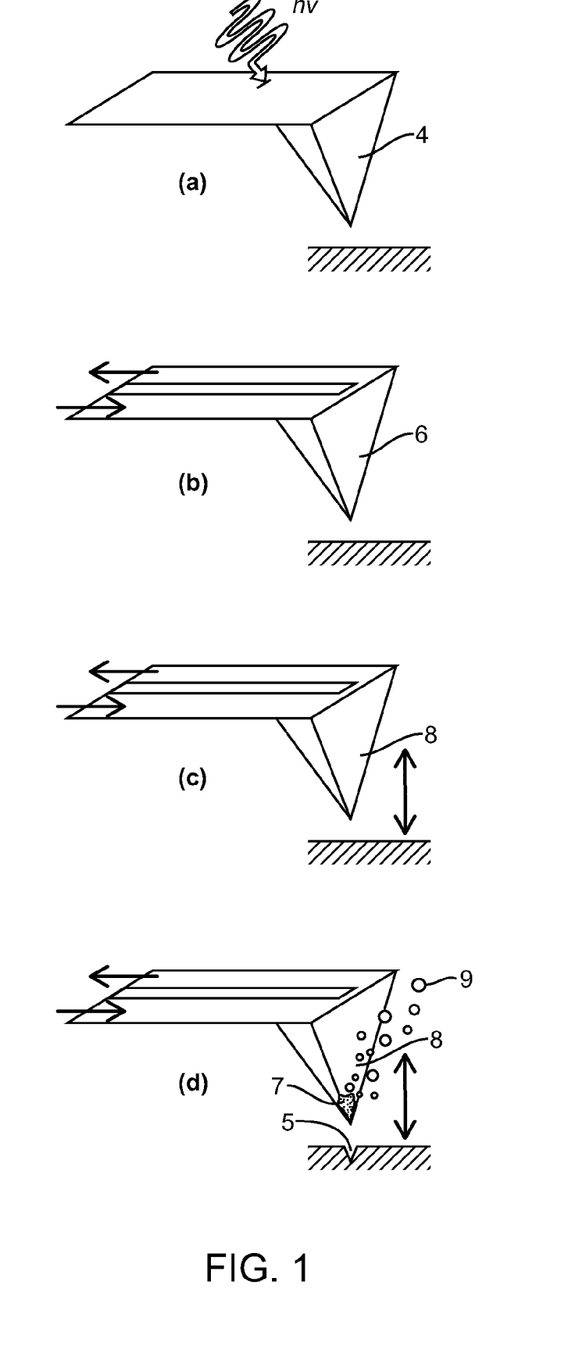

The heating step can be resistive heating. The heating can be by a probe having a rapidly heated tip that is heated by any suitable means. There is shown in FIG. 1(*a*) a probe 4 that is heated by a laser source. The heating of an alternative probe 6 can also be by a resistive element, as shown in FIG. 1(*b*). The resistive element heats the heating tip and thereby the sample surface. The resistive heating element can be solid state. The probe can be an atomic force microscopy cantilever. The cantilever probe 8 can then also provide rapid tapping, as shown in FIG. 1(*c*). Sample removal with the probe 8 will remove sample 7 from sample surface 5 as shown in FIG. 1 (*d*). The probe 8 can be heated when removed from the sample surface 5 to heat the sample 7 on the probe 8 and volatilize analyte 9.

The probe can have a heating tip having a surface area of less than 1 μm$^2$ in order to reduce the heat transfer area and improve the heating ramp rate. To reach $10^8$ K/s the cantilevers should be heated, for example, to 1000 K in 10 μs or less. Since the thermal diffusivity of pure silicon is 89×10$^{-8}$ m$^2$/sec, the time for heat to flow across a 1 μm thickness of cantilever that is 1 μm tall tip is 22 ns. A heating tip having a surface area of less than 1 μm$^2$ is therefore desirable to achieve 1000 K in 1 μs through the use of fast lock-in electronics.

The larger the volume of the heating filament the smaller the heating rate that can be achieved. Therefore, to inject heat into a surface at high speeds, very small heating elements must be used. Silicon based AFM probes that have tip diameters on the order of 20 nm and that are able to act as local resistive heaters can be used to achieve high heating rates. Commercially available heated AFM platforms that use heated probes can be utilized, such as those manufactured by Anasys Instruments Corporation (Santa Barbara, Calif.). Proper tip designs should allow at least also normal topography measurements with AFM. The control of AFM and the small tip sizes work together to enable imaging at the micrometer or better spatial resolution. The invention thereby can combine mass spectral imaging information and AFM derived imaging information from the same surface. This combined information can be processed by a suitably programmed processor.

The tip can be made of any suitable material. The material selection used for the tip can be optimized for the heating methodology. The tip must heat at the appropriate rate and to the highest temperature needed without deformation, melting, and outgassing. The tip should also be durable and last for repeated (thousands) of heating cycles without a change in performance. In one aspect, the tip can be constructed of silicon.

The tip can be heated to a temperature of between 0-1000° C. The tip can be heated in one aspect to at least 350° C. Some compounds will have to be heated higher than others, in addition to at a fast heating rate. The temperature will be selected to be that necessary for desorption of the particular compound. A temperature that is too high will result in some decomposition of the analyte. The maximum temperature can in one aspect be between 350° C. and 500° C., depending on the characteristics the compounds being analyzed. Maximum temperatures of up to 1000° C. or more are possible. The heating temperature and heating ramp rate can be selected such that desorption of the analyte takes place in 10 ns or less.

The analyte can be collected after it has been desorbed into the gas phase by any suitable method. The analyte can be drawn by a vacuum or directed by an inert gas carrier into an ionization region (ESI, APCI, APPI, ICP), ionized and then transferred into an analytical instrument such as a mass spectrometer for analysis. Alternatively the material liberated into the gas phase can be captured in a material trap or container for subsequent analysis. This permits concentration of the analyte for a subsequent desorption into another measurement device. It is additionally possible to obtain information about the analyte species captured by doing measurements of some kind on the sample surface, such as AFM measurements or other types of analysis.

The method can further comprise the step of ionizing the analyte after the analyte is desorbed. The analyzing of the analyte can be performed by any suitable method. The analyzing of the analyte can be performed using devices such as, but not limited to, mass spectrometers, ionization sources, spectroscopy devices, and separation methods. Other devices for analyzing the analyte could alternatively or additionally be used. The ionization sources can be any suitable ionization source, such as ESI, APCI, APPI, ICP, and ESCi. Other ionization sources are possible. Ionization does not have to occur at atmospheric pressure. The neutrals can be drawn into the instrument vacuum region and ionized by electron ionization or chemical ionization or photoionization.

The separation method can be at least one of liquid chromatography, solid phase extraction, HPLC, and capillary electrophoresis. Other separation methods are possible. Examples include ion mobility spectrometry or differential mobility spectrometry performed at atmospheric pressure or at reduced pressure. The mass spectrometer can be at least one selected from the group consisting of sector MS, time-of-flight MS, quadrupole mass filter MS, three-dimensional quadrupole ion trap MS, linear quadrupole ion trap MS, Fourier transform ion cyclotron resonance MS, orbitrap MS, and toroidal ion trap MS.

Figure 2:
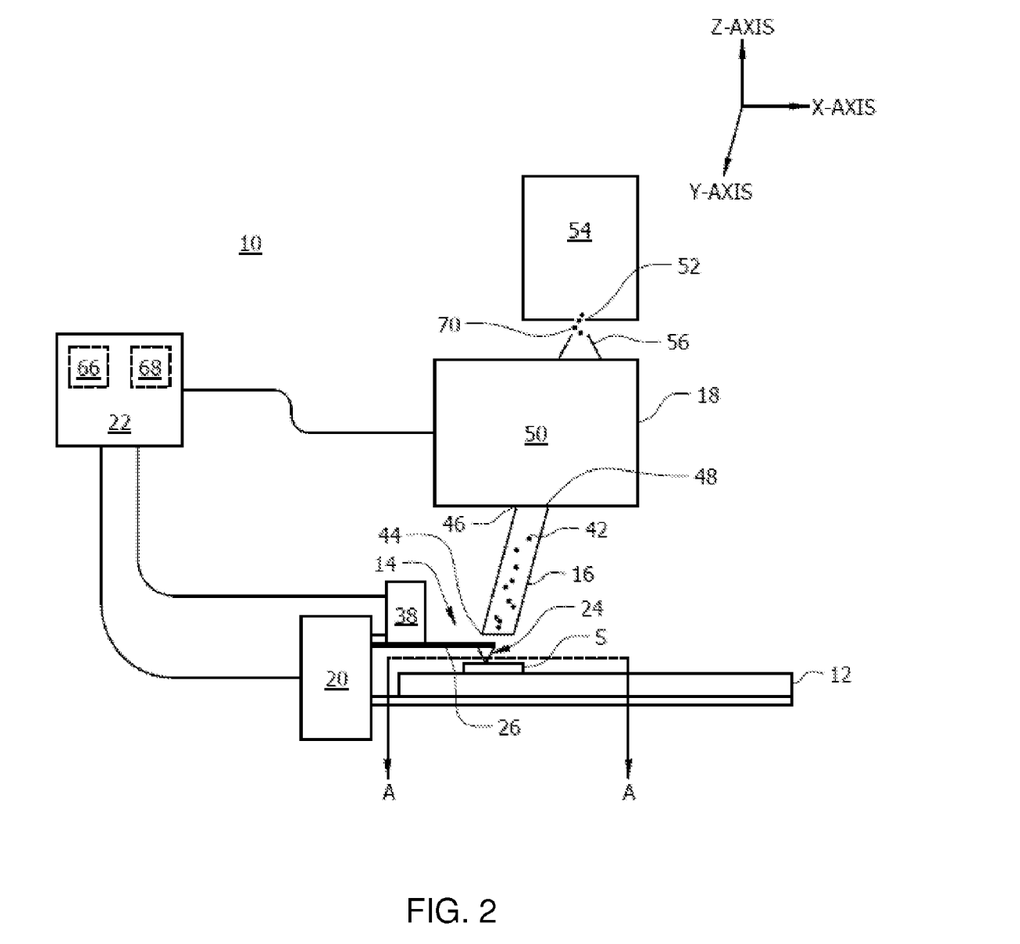
FIG. 2 is schematic diagram of a thermal desorption system suitable for use with the invention.
Figure 3:
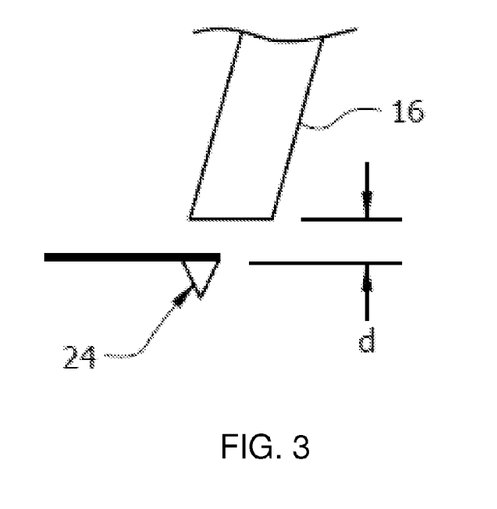
FIG. 3 is a cross section taken along line A-A in FIG. 2.

As shown in FIGS. 2-3, a system 10 for analyzing a chemical composition of a specimen (S) can include a sample stage 12 for supporting the specimen (S), a rapid-heating thermal desorption probe 14, a collection device 16, an analytical instrument 18, a stepper mechanism 20, and a controller 22. The stepper mechanism 20 can be configured to move the specimen stage 12 and the rapid-heating thermal desorption probe 14 relative to one another.

The rapid-heating thermal desorption probe 14 can include a thermally active tip 24 extending from a cantilever body 26. The thermally active tip 24 can include a distal end that has a conical shape with a rounded tip. The apex of the thermally active tip 24 can have a radius of 250 nm or less, or 100 nm or less, or 75 nm or less, or 50 nm or less, or 30 nm or less, or 15 nm or less. The thermally active tip 24 can be in communication with a heating mechanism such that the thermally active tip 24 can be heated to a temperature of at least 250° C., at least 350° C., at least 400° C., at least 450° C., at least 500° C., or at least 1000° C.

Figure 4:
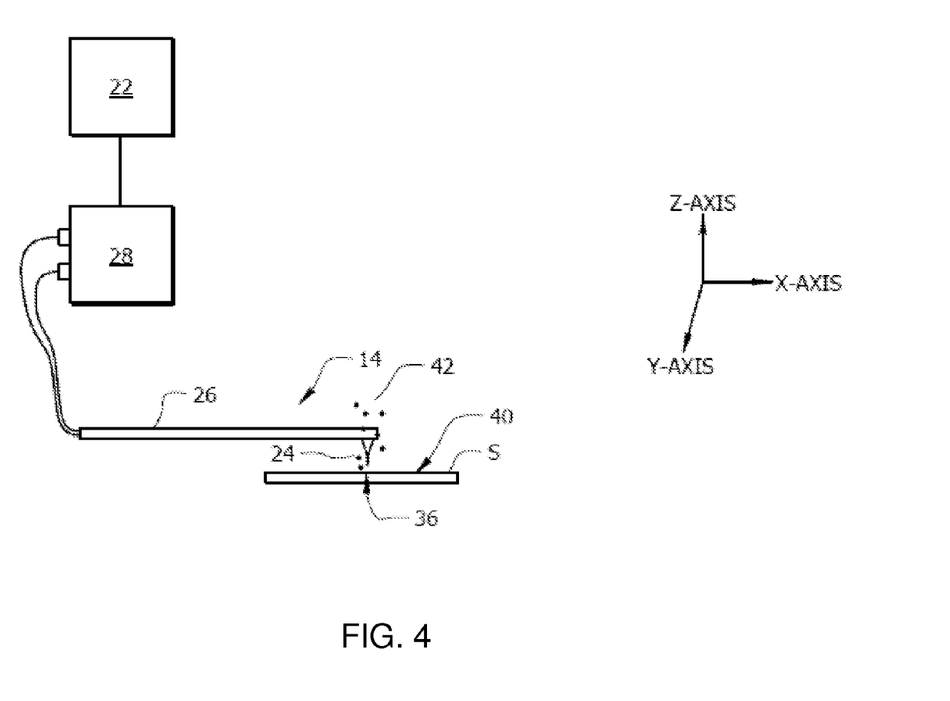
FIG. 4 is a schematic diagram of a resistively heated thermal desorption system according to the invention.

The heating mechanism can be a voltage source 28 connected to a resistive heating circuit coupled to the rapid-heating thermal desorption probe 14. In such an example, the voltage source can be electrically coupled to the resistive heating circuit of the rapid-heating thermal desorption probe 14 and the thermally active tip 24 can be heated via resistive heating.

Figure 5:
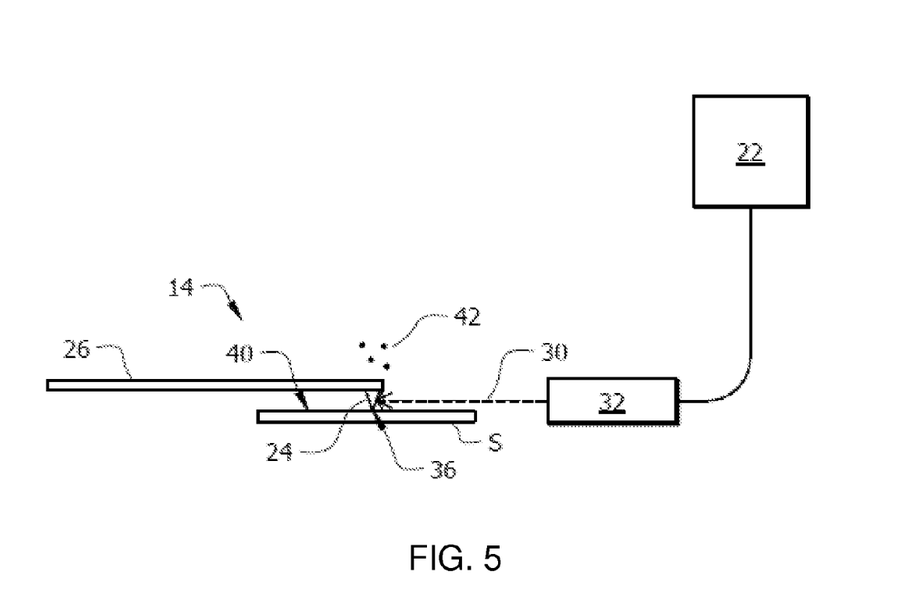
FIG. 5 is a schematic diagram of a laser heated thermal desorption system according to the invention.
Figure 6:
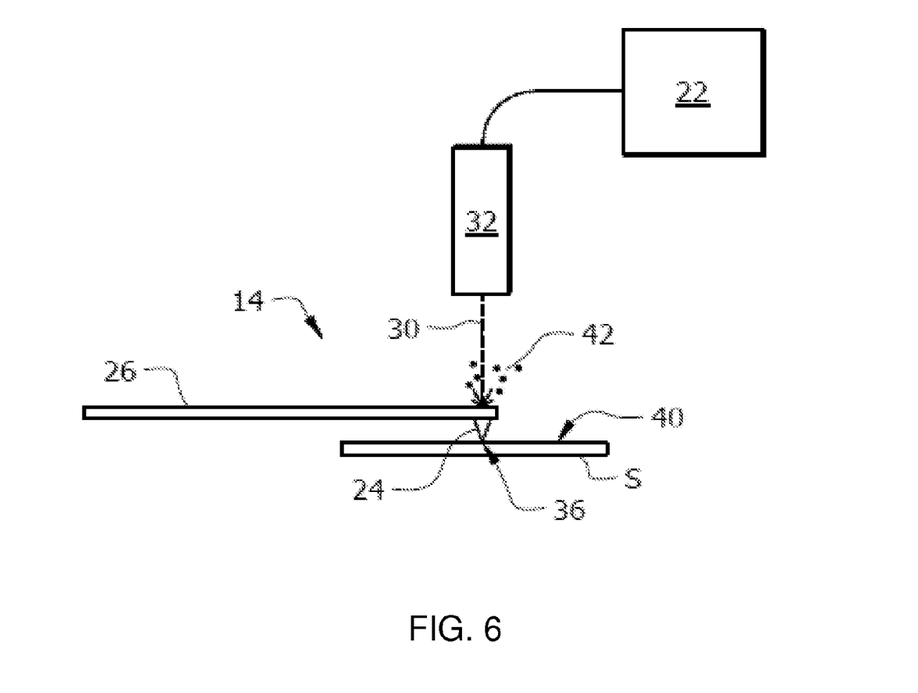
FIG. 6 is a schematic diagram of an alternative laser heated thermal desorption system according to the invention.

In another example, the heating mechanism can be a laser beam 30 emitted by a laser 32 and the heating can be facilitated by directing the laser beam 30 at the rapid-heating thermal desorption probe 14. In particular, the laser beam 30 can be directed at the thermally active tip 24 or the cantilever body 26, as shown in FIGS. 5 and 6, respectively.

Where the thermally active tip 24 contacts the specimen (S), the heating mechanism can include frictional force. For example, the cantilever body 26 can oscillate at a high frequency, e.g., an ultrasonic frequency, while the thermally active tip 24 contacts the specimen (S). The repeated contacting of the specimen (S) by the thermally active tip 24 can provide additional heating or can be used as an independent method of thermally desorbing the gaseous analyte 42 from the target site 36.

The rapid-heating thermal desorption probe 14 can also be designed to function as an atomic force microscopy probe. Thus, the mechanical properties of the thermal desorption probe 14 and its components, the thermally active tip 24 and the cantilever body 26, can be designed for use for measuring the topography of a surface as part of an atomic force microscope. The system 10 can include an atomic force microscopy system 38 for utilizing the thermal desorption probe 14 for measuring the topography of a surface 40 of the specimen S.

An inlet 44 of the collection device 16 can be positioned proximate the thermally active tip 24. For example, as shown in FIG. 3, a distance (d) between the inlet 44 of the collection device 16 and the thermally active tip 24 can be 500 µm or less, or 250 µm or less, or 100 µm or less, or 50 µm or less. In order to facilitate capture of the gaseous analyte 42, the collection device inlet 44 can be placed above the thermally active tip 24, as shown in FIG. 3. Because of the nanoscale dimensions of the thermally active tip 24, the quantity of gaseous analyte 42 evolved from an individual target site 36 is miniscule, e.g., on the order of picomoles or even attomoles. Alternatively, the collection device inlet 44 can be placed to the side of the thermally active tip 24.

During the analysis process, the optional stepper mechanism 20 can move the heated thermally active tip 24 and the target site 36 such that they are proximate to or in contact with one another. The rapid heating of the invention is applied until a gaseous analyte 42 evolves from the target site 36. The gaseous analyte 42 can include both volatized molecules from the target site 36, and pyrolytic decomposition products of molecules from the target site 36. The invention achieves intact volatilization of most or all of the larger molecules which in prior art systems resulted only in pyrolytic decomposition of these larger molecules.

The methods described herein can include maintaining the gaseous analyte 42 at a relatively constant temperature as the gaseous analyte 42 is transported from an inlet 44 to an outlet 46 of the collection device 16. For example, a temperature of the gaseous analyte 42 can be at least 150° C., at least 200° C., or at least 250° C., or at least 300° C., or at least 350° C. In particular, the temperature of the gaseous analyte 42 can be maintained high enough that the gaseous analyte 42 does not condense on an interior of the collection device 16.

An outlet 46 of the collection device 16 can coupled of an inlet 48 for an analytical instrument 18. An intake flow rate of the collection device 16 can be between 0.1 mL/min and 60 mL/min, or between 1 mL/min and 50 ml/min, or between 5 mL/min and 40 mL/min. The pressure at the sample surface can be approximately atmospheric pressure, e.g., 0.95-1.05 atm, or the sample can be contained within a vacuum to facilitate desorption and removal of the analyte. If the desorption takes place in a vacuum the ionization techniques should preferably be electron ionization (EI), chemical ionization (CI) or photoionization (PI). The ability to detect larger molecules could be reduced due to the state of current ionization technologies.

A gas outlet 46 of the collection device 16 can be coupled to a gas inlet 48 of an analytical instrument 18. For example, as shown in FIG. 2, the collection device 16 can be directly coupled to the gas inlet 48 of an ionization source 50 and indirectly coupled to the gas inlet 52 of a mass spectrometer 54. A gas outlet 56 of the ionization source 50 can be directly coupled to the gas inlet 52 of the mass spectrometer 54. As used herein, where an inlet and an outlet are coupled, they are physically coupled such that a gas exiting the outlet is directed into the inlet with little to no loss to the atmosphere. The analytical instrument 18 can be any instrument utilized for analyzing gaseous analytes.

The stepper mechanism 20 should be understood to include any device or combination of devices for changing the relative position between the thermal desorption probe 14 and the sample stage 12 or the specimen (S) supported thereon. For example, the sample stage 12 can be coupled to the stepper mechanism 20 and move the sample stage 12 laterally (X-axis), transversely (Y-axis), and vertically (Z-axis) along the sampling path 60. Alternately, the thermal desorption probe 14 can be mounted to the stepper 20, e.g., via the atomic force microscopy system 38, and can move the thermal desorption probe 14 laterally, transversely and vertically along the sampling path.

The thermal desorption can occur with the thermal desorption probe 14 in contact with the target site 36. The articulation between sequential target sites 36 can occur with the thermal desorption probe 14 in contact with the specimen (S) or proximate to, but not contacting, the specimen (S). Similarly, the thermal desorption can occur with the thermal desorption probe 14 proximate, but not contacting, the target site 36. The controller 22 can be configured for causing the stepper mechanism 20 to perform each of the thermal desorption sequences described above, or anywhere herein.

In some examples, the target sites 36 can be sampling lines. In general, the plurality of sampling lines will be parallel and spaced apart by a distance (dS). In such an embodiment, the specimen (S) can be thermally desorbed along an entire sampling line and the gaseous analyte 42 analyzed continuously by the analytical instrument 18. The thermal desorption probe and the sample stage 12 will then travel along a relocating path prior to thermally desorbing the next sampling line along the sampling path.

The sampling path can be an array of regularly spaced target sites. As used herein, "regular spacing" and "regularly spaced" are used interchangeably and refer to spacing where the distance between adjacent target sites in a line is equal or approximately equal along the length of the line. Regular spacing also refers to instances where the same target site is part of two or more lines with regular spacing. The center-to-center distance between adjacent target sites 36 can be 5 μm or less, or 3 μm or less, or 2 μm or less, or 1 μm or less, or 0.5 μm or less, or 250 nm or less, or 100 nm or less, or 50 nm or less.

In some instances, the entire sampling path will be determined prior to beginning the sampling process, i.e., prior to the thermal desorption of the first target site. In such instances, the surface of the specimen (S) can be scanned to determine the topography of the specimen (S) using the thermal desorption probe in atomic force microscopy mode. In such embodiments, the topography of the specimen (S) can be used to determine the lateral, transverse and vertical components of the sampling path prior to thermal desorption of the first target site.

The data from each of the target sites can be stored in a computer readable storage, such as are known in the art. The data can be complied to form a two-dimensional map, or surface, of the composition of the specimen by plotting the data according to the array of target sites was obtained. The data can be displayed on an output device, such as a monitor, printer, smartphone or the like.

The system 10 can also include a controller 22 configured for carrying out any of the method steps described herein. For example, the controller 22 can be configured for causing the stepper mechanism 20 to sequentially articulate the thermal desorption probe 14, the sample stage 12, or both, along a predetermined sampling path comprising a plurality of target sites. The controller 22 can also be configured for heating the rapid-heating tip 14 to the desired temperature at the desired ramp rate.

The controller 22 can include a computer readable storage 66 in communication with a processor 68. The computer readable storage 66 can include computer executable instructions for carrying out the methods described herein. The processor 68 can be configured to execute the computer executable instructions stored on the computer readable storage 66. The controller 22 can be in communication with the stepper mechanism 20, the atomic force microscopy system 38, the analytical instrument 50, the laser 32, the voltage source 28, and other components of the system. In addition, although shown as a single box that includes a single computer readable storage 66 and a single processor 68, it should be understood that the controller 22 can be spread across multiple devices and can include multiple computer readable storages and processors.

A method of analyzing a chemical composition of a specimen is also described. The method can include providing a specimen (S) for evaluation and a rapid-heating thermal desorption probe 14. The method can also include thermally desorbing an analyte from a target site 36 of the specimen (S) using a thermally active tip 24 of the rapid-heating thermal desorption probe 14 to form a gaseous analyte 42. The thermal desorption step can include heating the thermally active tip to above the desired desorption temperature at the desired ramp rate, and positioning the target site 36 and the thermally active tip 24 such that the heating step evolves the gaseous analyte 42. The method can also include ionizing the gaseous analyte 42 to form an ionized analyte 70 and analyzing a chemical composition of the ionized analyte 70.

The method can also include determining a predetermined sampling path comprising a plurality of target sites prior to the first thermal desorption step. Additionally, the method can include sequentially articulating the thermally active tip 24 and/or the sample stage 12 along the predetermined sampling path and repeating the thermally desorbing, ionizing and analyzing steps for each target site. The sequentially articulating step can include moving the thermally active tip 24, the sample stage 12 or both, so that the thermally active tip 24 is sequentially positioned proximate each target site along the sampling path so that each target site can be thermally desorbed.

The step of determining the predetermined sampling path can include analyzing the topography of the specimen utilizing the thermal desorption probe 14 in an atomic force microscopy mode. Analyzing can include mapping the position laterally and transversely and, optionally, vertically of the target sites and the sampling path.

The method can also include plotting any exogenous or endogenous property related to the specimen (S) being evaluated, including a property of a molecule or chemical component for each of the target sits. Properties of interest include, but are not limited to, concentration of a molecule or decomposition product, the relative ratio of two molecules (such as compound and reaction product of the compound), and the relative ratio of decomposition products.

For example, the property can be the concentration of a chemical component, such as a pharmaceutical and its metabolites, at each target site. By arranging the data for each target site spatially within the specimen (S) a two dimensional surface can be plotted.

Electrospray ionization (ESI) works by ionizing a gaseous sample through reaction with charged solvent droplets, protonated solvent species, or gas phase ions created in the ESI process. Besides the apparent high secondary ionization efficiency, the other advantage of using ESI is the ability to form multiply-charged species from macromolecular species.

In atmospheric pressure chemical ionization (APCI) ionization occurs by ion/molecule chemistry in a plasma that is created by a corona-discharge at the end of a metal needle. APCI is limited to forming singly-charged ions. The ionized molecules formed with either source will then be analyzed by either a quadrupole ion trap or a triple quadrupole mass spectrometer.

FIG. 2 shows an experimental set-up for the thermal desorption process described herein. Once the material is desorbed by the thermally active tip 24 the gaseous analyte 42 will be transferred from the desorption area 36 around the heated probe to the ionization source 50 using a pump that creates a flow of gas from the collection device inlet 44 into the ionization source 50. The gaseous analyte 42 will then be ionized by the ionization source (ESI or APCI) best suited for the targeted small molecule being investigated The invention provides very fast desorption times which can have other benefits such as a higher concentration of material that will be liberated as a pulse in a short period of time. The concentration of the analyte will be greater than the low concentrations that are obtained using constant temperature or slow temperature ramp methods. The invention can thereby improve detection limits.

This invention can be embodied in other forms without departing from the spirit or essential attributes thereof. Accordingly, reference should be made to the following claims to determine the scope of the invention.

We claim:

1. A method for analyzing a sample having at least one thermally labile analyte, comprising the steps of:
    heating the sample at a rate of at least $10^6$ K/s, to thermally desorb at least one thermally labile analyte from the sample;
    collecting the desorbed thermally labile analyte; and
    analyzing the thermally labile analyte;
    wherein the heating is by a probe having a resistive heating element; and
    placing the probe tip into and out of contact with the surface with a drive.

2. The method of claim 1, wherein the heating rate is at least $10^{13}$ K/s.

3. The method of claim 1, wherein the heating rate is between $10^6$-$10^{13}$ K/s.

4. The method of claim 1, wherein the thermally labile analyte has a molecular weight of greater than 500 Da.

5. The method of claim 1, wherein the thermally labile analyte has a molecular weight greater than 1000 Da.

6. The method of claim 1, wherein the heating step is resistive heating.

7. The method of claim 1, wherein the heating is by a probe having a resistive heating element.

8. The method of claim 7, wherein the probe has a heating tip having a surface area of less than 1 $\mu m^2$.

9. The method of claim 8, wherein the tip is silicon.

10. The method of claim 7, wherein the resistive heating element is solid state.

11. The method of claim 7, wherein the probe is an atomic force microscopy cantilever.

12. The method of claim 1, further comprising the step of ionizing the thermally labile analyte after the analyte is desorbed.

13. The method of claim 1, wherein the step of analyzing the analyte is performed by at least one selected from the group consisting of mass spectrometers, ionization sources, spectroscopy devices, and separation methods.

14. The method of claim 13, wherein the ionization sources are at least one selected from the group consisting of electrospray ionization, atmospheric pressure chemical ionization, electrospray chemical ionization (ESCi), atmospheric pressure photo-ionization, and inductively coupled plasma.

15. The method of claim 13, wherein the separation method is at least one selected from the group consisting of liquid chromatography, solid phase extraction, HPLC, capillary electrophoresis, ion mobility spectrometry and differential mobility spectrometry.

16. The method of claim 13, wherein the mass spectrometer is at least one selected from the group consisting of sector MS, time-of-flight MS, quadrupole mass filter MS, three-dimensional quadrupole ion trap MS, linear quadrupole ion trap MS, Fourier transform ion cyclotron resonance MS, orbitrap MS, and toroidal ion trap MS.

17. The method of claim 1, wherein the sample is heated at a sample surface.

18. The method of claim 1, wherein the sample is removed from a sample surface and then heated.

19. A method for collecting an thermally labile analyte from a sample, comprising the steps of
    heating the sample at a rate of at least $10^6$ K/s to thermally desorb at least one thermally labile analyte from the sample; and,
    collecting the desorbed thermally labile analyte;
    wherein the heating is by a probe having a resistive heating element; and
    placing the probe tip into and out of contact with the surface with a drive.

20. A system for collecting a sample having at least one thermally labile analyte, comprising:
    a tip having a resistive heating device heating the tip at a rate of at least $10^6$ K/s to thermally desorb the at least one thermally labile analyte from the sample;
    a drive for placing the tip into and out of contact with the surface; and,
    means for collecting the thermally labile analyte.

21. The system of claim 20, wherein the heating device comprises a resistive element.

22. The system of claim 20, wherein the heating device comprises a laser.

23. The system of claim 20, further comprising a vacuum pump and a device for ionizing the analyte in a vacuum comprising at least one selected from the group consisting of an electron ionization (EI), chemical ionization (CI) or photoionization (PI) device.

* * * * *